(12) United States Patent
Cigaina et al.

(10) Patent No.: US 10,952,770 B2
(45) Date of Patent: Mar. 23, 2021

(54) IMPLANTATION TOOL FOR IMPLANTING A TOTALLY IMPLANTABLE DEVICE IN THE BODY OF A HUMAN OR ANIMAL

(71) Applicant: MedAutonomic SRL, Venezia Mestre (IT)

(72) Inventors: Valerio Cigaina, Cortina d'Ampezzo (IT); Paolo Fabris, Thiene (IT); Simone Cigaina, Villorba (IT)

(73) Assignee: MedAutonomic S.r.L., Venezia Mestre (IT)

(*) Notice: Subject to any disclaimer, the term of this patent is extended or adjusted under 35 U.S.C. 154(b) by 289 days.

(21) Appl. No.: 16/087,690

(22) PCT Filed: May 11, 2017

(86) PCT No.: PCT/EP2017/061300
§ 371 (c)(1),
(2) Date: Sep. 24, 2018

(87) PCT Pub. No.: WO2017/198532
PCT Pub. Date: Nov. 23, 2017

(65) Prior Publication Data
US 2020/0297380 A1 Sep. 24, 2020

(30) Foreign Application Priority Data

May 18, 2016 (IT) .................... 102016000051230

(51) Int. Cl.
*A61B 17/34* (2006.01)
*A61N 1/05* (2006.01)
(Continued)

(52) U.S. Cl.
CPC ........ *A61B 17/3468* (2013.01); *A61N 1/0507* (2013.01); *A61N 1/36007* (2013.01);
(Continued)

(58) Field of Classification Search
CPC .......... A61B 17/3463; A61B 2217/007; A61N 1/0507; A61N 1/04; A61N 1/37205
See application file for complete search history.

(56) References Cited

U.S. PATENT DOCUMENTS 6,338,345 B1 * 1/2002 Johnson ........... A61B 17/12022
128/897
6,699,263 B2 * 3/2004 Cope .................. A61B 17/0401
606/153

(Continued)

FOREIGN PATENT DOCUMENTS

WO 2015079005 A1 6/2015

OTHER PUBLICATIONS

International Search Report dated Aug. 16, 2017; International Application No. PCT/EP2017/061300; International Filing Date May 11, 2017; 4 pages.

(Continued)

*Primary Examiner* — Alexander J Orkin
(74) *Attorney, Agent, or Firm* — Blank Rome LLP (57) ABSTRACT

An implantation tool (2) for implanting a totally implantable device (1) in the body of a human or animal, comprising an axially hollow needle (13) connected to a supply conduit (16) for a fluid injectable from said needle (13) for the creation of a tissue swelling (4), into which said device (1) is introducible, a longitudinal containment body (6) having inside it an axial cavity along which the needle (13) is slidingly guided, and a pulling element (11) disengageably engaged to said containment body (6) for drawing and releasing said device (1) in said tissue swelling (4).

20 Claims, 6 Drawing Sheets

(51) Int. Cl.
*A61N 1/36* (2006.01)
*A61B 17/00* (2006.01)

(52) U.S. Cl.
CPC .............. *A61B 2017/00269* (2013.01); *A61B 2017/3464* (2013.01); *A61B 2217/007* (2013.01)

(56) References Cited

U.S. PATENT DOCUMENTS

| | | | |
|---|---|---|---|
| 7,185,657 B1 | 3/2007 | Johnson et al. | |
| 7,909,851 B2* | 3/2011 | Stone | A61B 17/0482 606/232 |
| 8,105,342 B2* | 1/2012 | Onuki | A61B 17/0469 606/139 |
| 2002/0165589 A1 | 11/2002 | Imran et al. | |
| 2006/0095079 A1* | 5/2006 | Gerber | A61N 1/372 607/2 |
| 2006/0142789 A1* | 6/2006 | Lehman | A61B 17/3468 606/153 |
| 2007/0021736 A1* | 1/2007 | Johnson | A61B 17/0401 606/1 |
| 2008/0208219 A1* | 8/2008 | Suzuki | A61B 17/0487 606/144 |
| 2009/0076521 A1* | 3/2009 | Hansen | A61N 1/05 606/129 |
| 2010/0145352 A1 | 6/2010 | Chang et al. | |
| 2010/0324644 A1 | 12/2010 | Levi et al. | |
| 2013/0218229 A1 | 8/2013 | Sharma | |

OTHER PUBLICATIONS

Written Opinion dated Aug. 16, 2017; International Application No. PCT/EP2017/061300; International Filing Date May 11, 2017; 4 pages.

* cited by examiner

Figura 2a

Figura 2b

Figura 2c

Figura 5

Figura 7d  Figura 7c  Figura 7b  Figura 7a

Figura 7g  Figura 7f  Figura 7e

Figura 8a

Figura 8b

Figura 8c

IMPLANTATION TOOL FOR IMPLANTING A TOTALLY IMPLANTABLE DEVICE IN THE BODY OF A HUMAN OR ANIMAL

The present invention relates to an implantation tool for implanting a totally implantable device in the body of a human or animal.

The field of application extends to an implantation tool for implanting any device that can be housed in the gastric wall, within or beneath the submucosa or in the thickness of the wall of the entire digestive tract and/or any hollow organ or within walls on the inside or outside of the body of a human or animal.

Patent application WO 2015/079005 discloses an implantation tool for implanting a totally implantable device.

The implantation tool described in WO 2015/079005 is capable of facilitating the operations of inserting and positioning any device whatsoever, without the need for surgical intervention under general anaesthesia and the associated consequences, e.g. hospitalisation.

The implantation tool described in WO 2015/079005 provides for the device to be pushed into the implant site by means of a special pushing system.

However, this implantation tool is not completely effective in some situations, for example in the case of redundant gastric mucosa, which does not allow the tool to perforate the surface thereof. The technical task of the invention is to overcome the limits of said system, as well as to enable implantation also in other organs, besides the stomach, that are difficult to reach.

The technical task, as well as these and other objects, according to the present invention, are achieved by devising an implantation tool for implanting a totally implantable device in the body of a human or animal, characterised in that it comprises an axially hollow needle connected to a supply conduit for a fluid injectable from said needle for the creation of a tissue swelling, into which said device is introducible, a longitudinal containment body having inside it an axial cavity along which said needle is slidingly guided, and a pulling element disengageably engaged to said longitudinal body for drawing and releasing said device in said tissue swelling. The basic idea of the invention therefore consists in providing a tool configured to draw rather than push the device to the implant site in order to overcome the problems tied to the difficulty of perforating the gastric mucosa and thus penetrating into the gastric wall.

The implantation tool is thus capable of delivering any device whatsoever into the thickness of the gastric wall, or into the thickness of the wall of the entire digestive tract or any hollow organ or cavity of the body or within walls of the body of a human or animal.

Preferably, the needle for creating the tissue swelling is floating.

Preferably, the needle is driven in movement by the supply conduit of the needle itself. The needle incorporated in the said containment body has a tip that projects in front of a tapered front end of said containment body.

The tapered front end of the containment body mates the shape the needle so as to facilitate entry into the tissue.

Furthermore, the front end of the containment body has a blunt, non-cutting shape so as to facilitate the detachment of the tissue while avoiding the risk of cutting or tearing it when the needle is in a retracted position inside the containment body.

Preferably, the needle extends along the axial generatrix of the containment body that passes through the forwardmost point of the front end of said containment body.

The implantation tool can be used either on its own, for example for implants on the outside of the body of a human or animal, or coupled with any endoscopic instrument for implants inside the body of a human or animal.

Preferably, said pulling element extends outside said containment body.

Said pulling element can be made up of a flexible plate provided at one end with an eyelet for the passage of the needle, or a cable.

Said cable can be eyelet-shaped or can alternatively also be an open cable with splices at the ends.

Preferably, said needle has an extraction position in which it is extracted with its tip from the front end of the containment body, a position of partial retraction in which it is completely retracted into the front end of the containment body and engages said pulling element, and a position of complete retraction in which it is completely retracted into the front end of the containment body and frees said pulling element.

Preferably, said containment body has an elastically yielding stop for stopping said needle in said position of partial retraction into said containment body.

The needle for creating the tissue swelling can therefore be positioned on three different levels: (i) totally exposed, i.e. when it is in a completely forward position, to enable it to penetrate the target layer of the implant; (ii) in a partially rearward position from which it no longer protrudes from the tip of the containment body, but which still enables the retention of the pulling element of the device to be implanted; (iii) in a totally rearward position, with the freeing of the pulling element of the device to be implanted.

Preferably, at least the extracted position and the partially retracted position of the needle correspond to a respective mechanical interference, so that the operator can have clear evidence of having reached the desired position.

Preferably, the supply conduit of the needle is made up of a flexible tube contained in a flexible sheath imparting mechanical strength in an axial direction.

The positioning of the device within a biological tissue comprises, in sequence, the steps of:
  engaging the device to said implantation tool and drawing it into a pre-established implantation tissue area;
  extracting said needle from said containment body and creating an implant site, supplying said needle with a quantity of fluid that is injected into said tissue area so as to create a circumscribed tissue swelling which acts as an implant site;
  making the front end of the containment body penetrate into the implant site thus created;
  retracting the needle into the containment body and making the containment body penetrate further below the tissue so as to facilitate the detachment thereof from the underlying surface;
  continuing the penetration until drawing the device into the implant site;
  once the device is completely inside the implant site, disengaging the device from the pulling element and selectively retracting the tool, leaving the implant in the implant site.

The fluid used to create the implant site can be distilled water or a saline solution or medicated solution.

Additional features and advantages of the invention will become more apparent from the description of a preferred, but non-exclusive embodiment of the implantation tool according to the invention, illustrated by way of non-limiting example in the appended drawings, in which.

Equivalent parts in the various embodiments of the invention will be indicated with the same reference number.

The implantation tool 2 comprises a system 3 for creating a circumscribed tissue swelling 4, into which the device 1 is introducible, and a system 5 for inserting the device 1 into the swelling 4, which can be created in the gastric mucosa or in other soft tissues or in the thickness of the entire digestive system or any hollow organ or cavity or within walls on the inside or outside of the body of a human or animal.

The system 3 for creating the tissue swelling 4 comprises an axially hollow needle 13 connected to a supply conduit 16 for a fluid injectable from the needle 13 for the creation of the tissue swelling 4.

The conduit 16 is made up of a flexible tube wrapped in a flexible axial stiffening sheath 18, which is made up, in particular, of a pre-loaded coil spring in order to simultaneously impart to the insertion system 5 a good flexibility and a sufficient rigidity in a longitudinal direction, rigidity that is necessary for penetrating the target tissue of the implant.

The end 15 of the supply conduit 16 is inserted into a rear connector 17 of a containment body 6 and is fitted over the rear end of the needle 13.

One end of the sheath 18 is likewise inserted into the rear connector 17 of the containment body 6.

The system 5 for inserting the device 1 into the swelling 4 comprises the longitudinal containment body 6 having inside it an axial cavity 22 along which the needle 13 is slidingly guided, and a pulling element 11 disengageably engaged to the longitudinal body 6 for drawing and releasing the device 1 in the tissue swelling 4.

The containment body 6 has a external cylindrical conformation with a tapered, e.g. truncated cone-shaped, front end, from which the tip 14 of the needle 13 can exit.

The edge of the front end 7 of the containment body 6 is not sharp, but rather slightly rounded in order to facilitate the detachment of the tissue subjected to swelling.

The needle 13 extends along the axial generatrix of the containment body 6 that passes through the most forward point of the front end 7 of the containment body 6 itself.

The axial cavity 22 of the containment body also has a cylindrical conformation.

The needle 13 is floating and is movable by a drive system, not shown, which acts on the supply conduit 16.

The pulling element 11 extends outside and laterally to the containment body 6 and, with reference to FIGS. 1-8c, it is made up of a closed, openable eyelet-shaped cable 12, whereas with reference to FIGS. 9-14 is made up of a flexible plate 23 that extends from one end of the device 1.

With reference to FIGS. 1-8c, the containment body 6 has a housing seat 8 which originates from the outer surface thereof and extends through the axial cavity 22 in order to releasably retain one end of the cable 12. The housing seat 8 is delimited by a slot 27 which extends substantially in a plane that obliquely intersects the longitudinal axis of the containment body 6. The containment body 6 has an additional housing seat 9 for permanently retaining the other end of the cable 12.

With reference to FIGS. 9-14, the containment body 6 instead has a transverse slot 28 which transversally intersects the axial cavity 22. The plate 23 has an end which is insertable in the slot 28 and has an eyelet 30 for the passage of the needle 13.

The needle 13 has an extraction position in which it is extracted with its tip 14 from the front end of the containment body 6 and retains the pulling element 11, a position of partial retraction in which it is completely retracted into the front end of the containment body 6 and retains the pulling element 11, and a position of complete retraction in which it is completely retracted into the front end of the containment body 6 but no longer retains the pulling element 11. With reference to FIGS. 1-8c, in the positions of extraction and partial retraction the needle 13 engages the housing seat 8 to retain the releasable end of the cable 12, whereas in the position of complete retraction it disengages the housing seat 8 to release the releasable end of the cable 12. With reference to FIGS. 9-14, in the positions of extraction and partial retraction the needle 13 engages the eyelet 30 to retain the plate 23, whereas in the position of complete retraction it disengages the eyelet 30 to release the plate 23.

The containment body 6 further has an elastically yielding stop 10 for stopping the needle 13 in the position of partial retraction into the containment body 6.

The stop 10 is positioned at the end of a flexible longitudinal tab 25 connected at the other end to the containment body 6.

The longitudinal tab 25 is obtained from the containment body 6 itself and in particular it is delimited by a longitudinal slot 26 which originates on the outer surface of the containment body 6 and extends inside the containment body 6 in a frontward direction of the containment body 6. When the stop 10 intercepts the connector 15, it provides the operator with an indication of having reached the correct position of partial retraction of the needle 13.

Figure 2A:
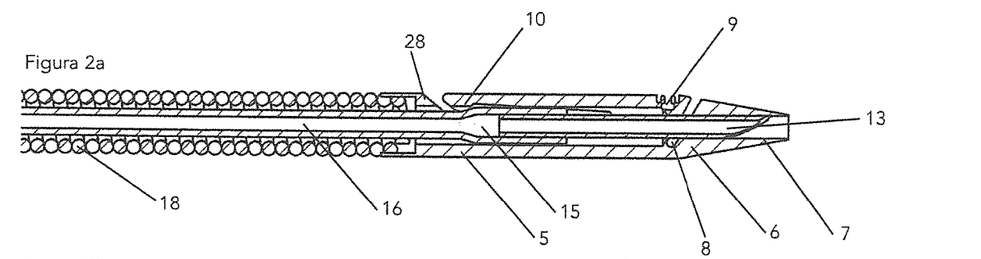
FIGS. 2a-2c show, respectively, a sectional, plan and side elevation view of the implantation tool with the needle in a partially retracted position and the implant still engaged to the pulling element.
Figures 2B, 2C:
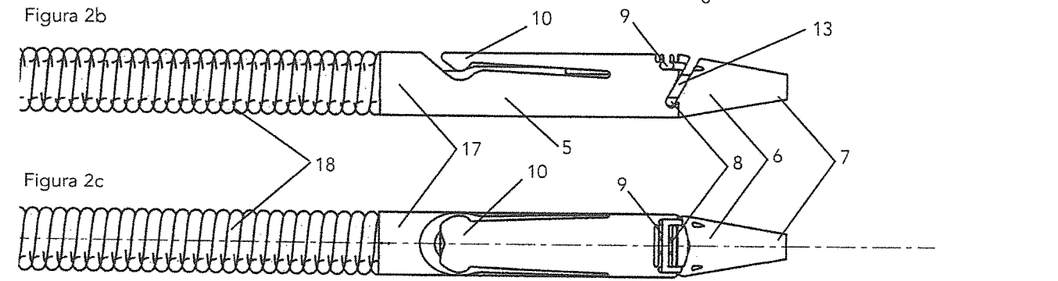
Figure 3A:
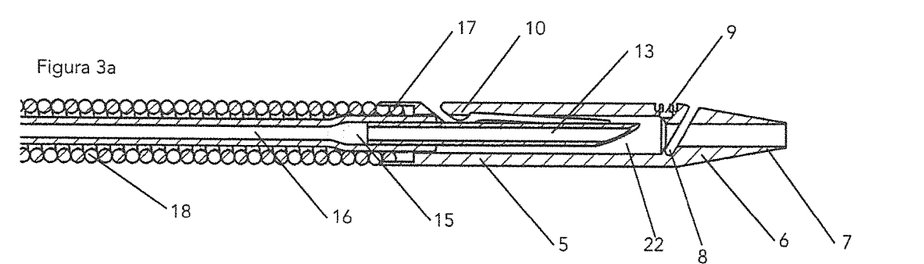
FIGS. 3a-3c show, respectively, a sectional, plan and side elevation view of the implantation tool with the needle in a completely retracted position and the implant disengaged from the pulling element.
Figures 3B, 3C, 6:
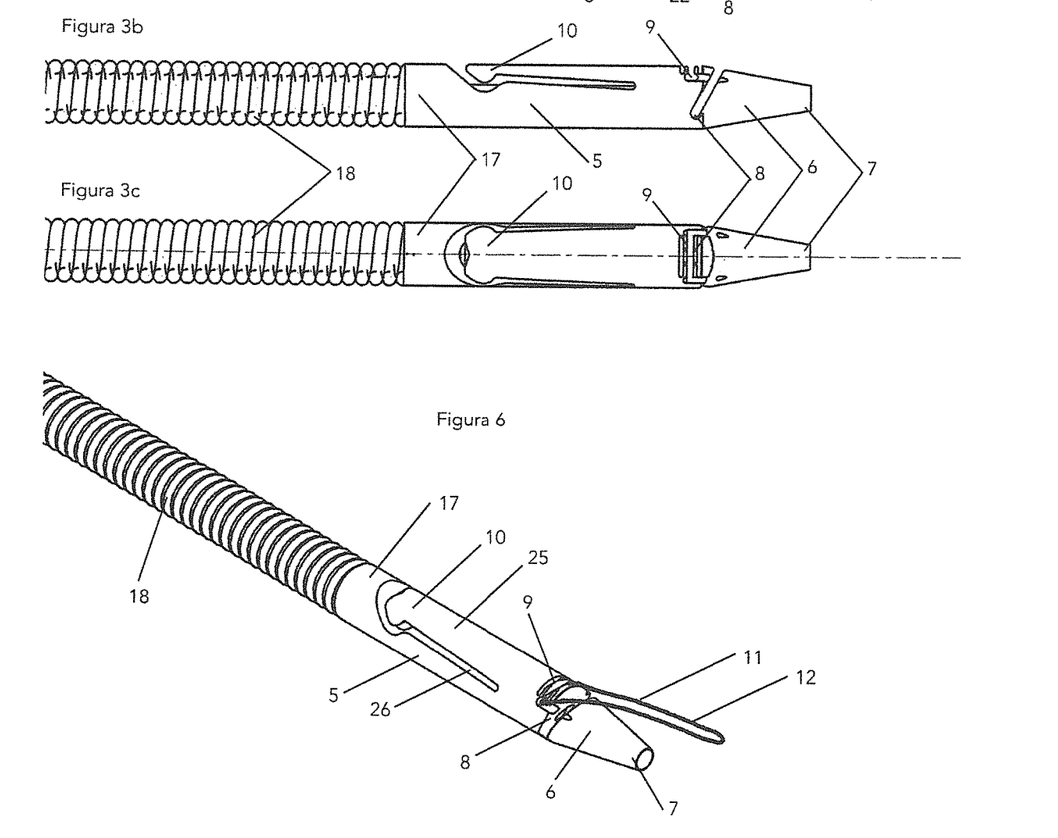
FIG. 6 shows an axonometric view of the implantation tool as shown in FIG. 3, including the pulling element.
Figure 4:
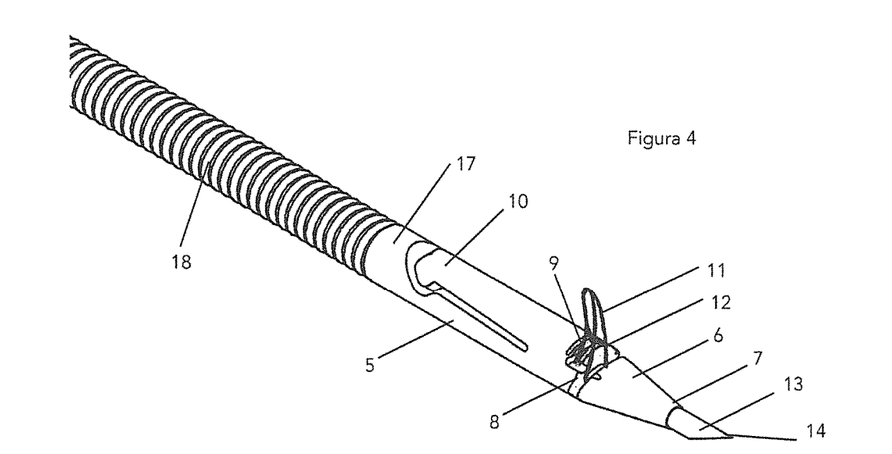
FIG. 4 shows an axonometric view of the implantation tool as shown in FIG. 1, including the pulling element.
Figure 5:
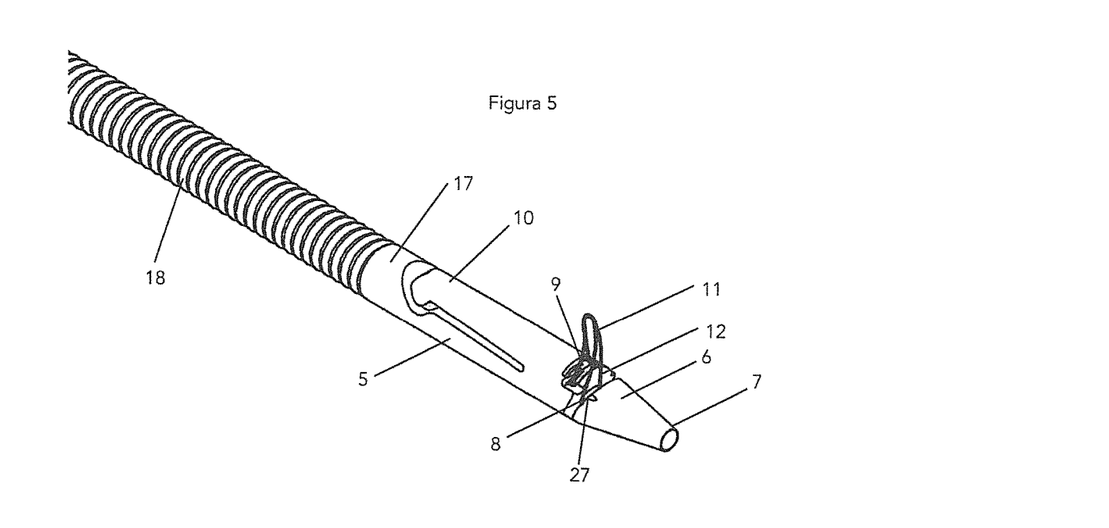
FIG. 5 shows an axonometric view of the implantation tool as shown in FIG. 2, including the pulling element.
Figures 7A, 7B:
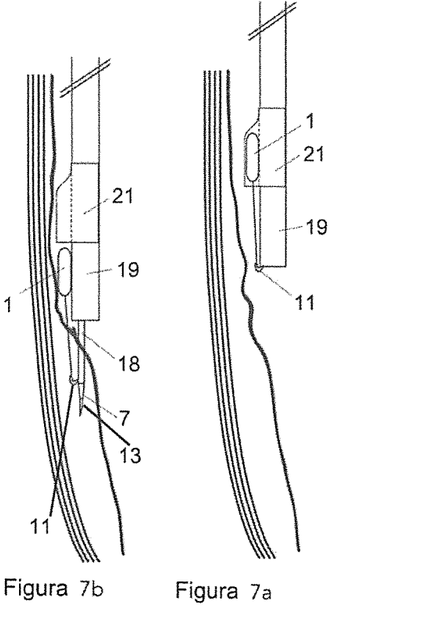
FIGS. 7a, 7b, 7c, 7d, 7e, 7f and 7g show the sequence of use of the implantation tool in the case of use with an endoscope.
Figure 7C:
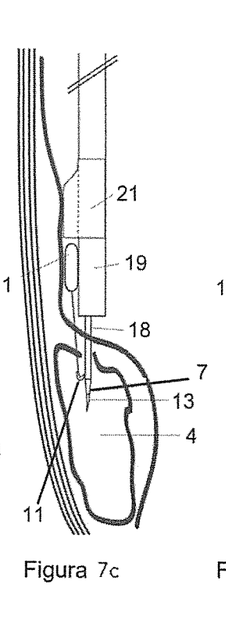
Figure 7D:
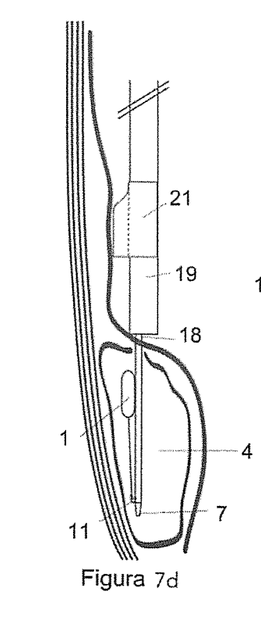
Figure 7E:
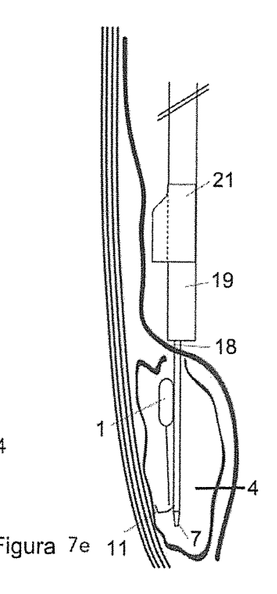
Figure 7F:
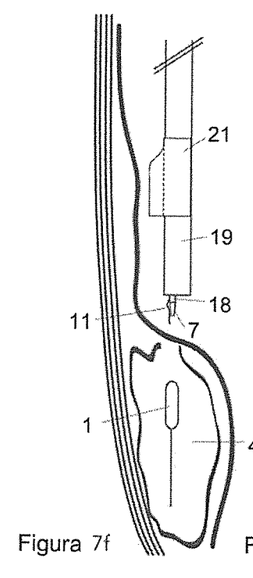
Figure 7G:
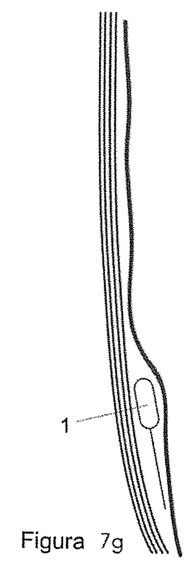

If, from that position, a further pull is exerted on the drive system of the system 3 relative to the position illustrated in FIGS. 2a-2c, the connector 15 bends the stop 10 until passing over it, thus permitting the needle 13 to reach the position of complete retraction, which corresponds to the release of the pulling element 11 and consequently the possibility of releasing the device 1 to be implanted.

Between the inner wall of the insertion system 6 and the outer wall of the system 3 for creating the tissue swelling, a fluid-tight sealing means is provided, for example a toroidal gasket, to prevent the return of organic fluid or of the fluid injected via the needle 13 during penetration of the tool 2 into the tissue and during the creation of the tissue swelling 4.

Figure 8A:
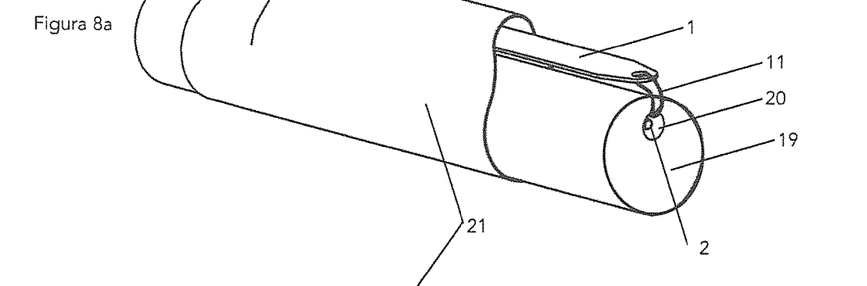
FIGS. 8a-8c show the sequence of movement of the implantation tool in the application in which it is coupled to an endoscope.
Figure 8B:
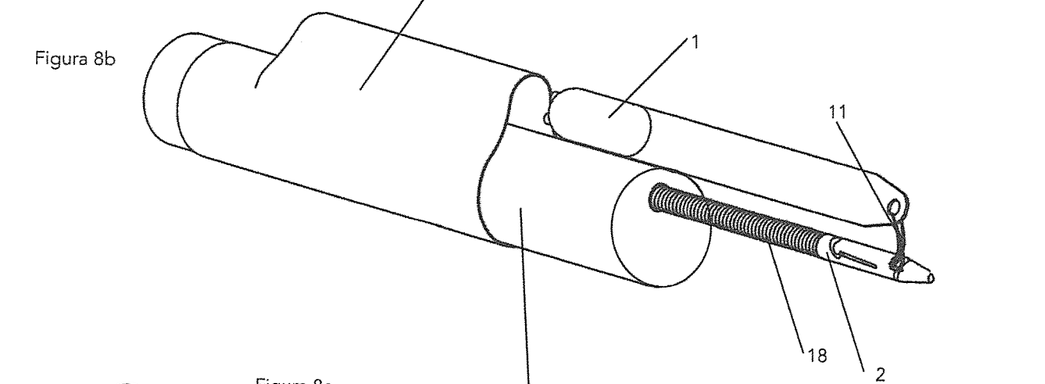
Figure 8C:
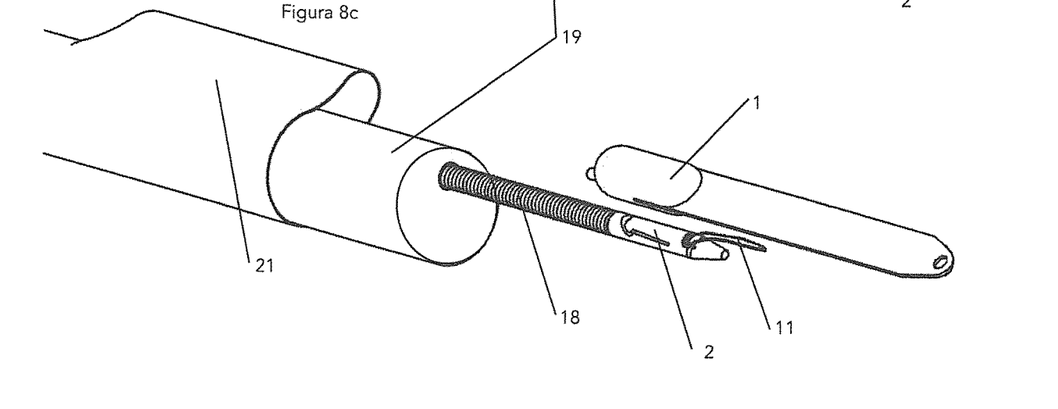
Figures 9, 10, 11, 12, 13:
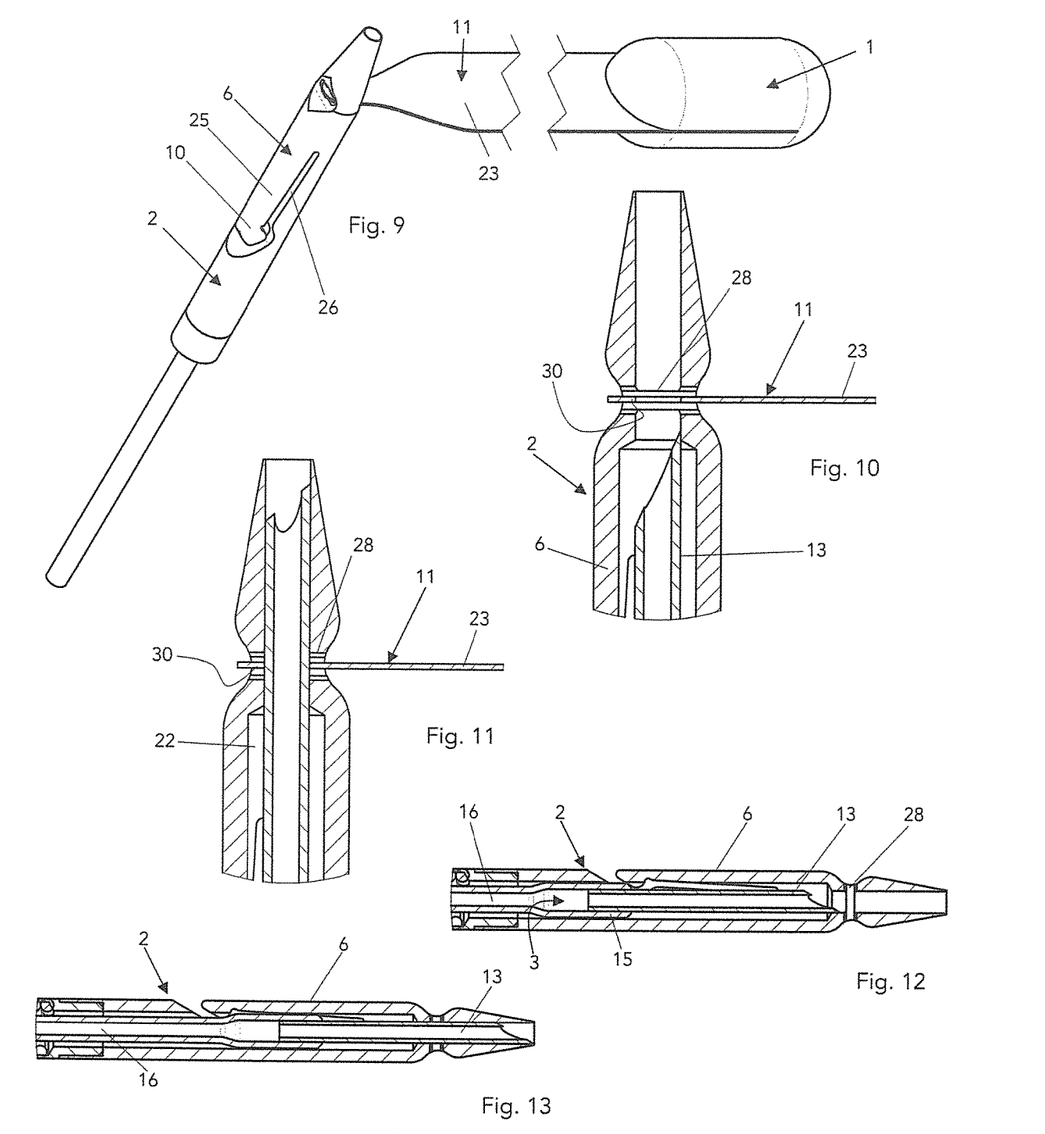
FIG. 9 shows the implantation tool in a variant of the pulling system of the device.
FIG. 10 shows a sectional view of a part of the implantation tool of FIG. 9, with the needle disengaged from the pulling element.
FIG. 11 shows a sectional view of a part of the implantation tool of FIG. 9, with the needle engaged in the pulling element but still retracted in the containment body.
FIG. 12 shows a sectional view of a part of solely the implantation tool of FIG. 9, with the needle in a position of disengagement from the pulling element.
FIG. 13 shows a sectional view of a part of solely the implantation tool of FIG. 9, with the needle retracted in the containment body and in a position of engagement with the pulling element.
Figure 14:
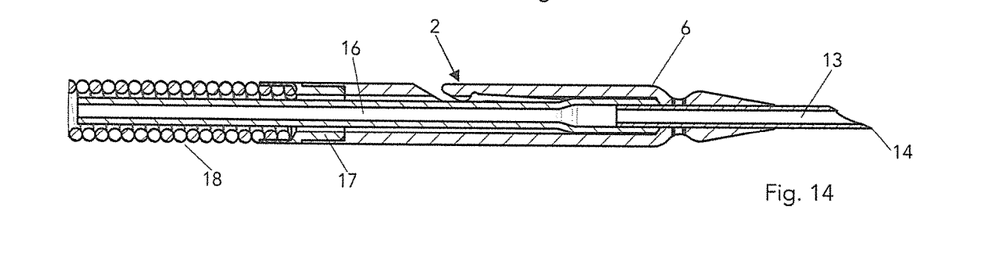
FIG. 14 shows a sectional view of a part of solely the implantation tool of FIG. 9, with the needle projecting from the containment body and in a position of engagement with the pulling element.

The assembly comprising the device 1 and the tool 2 can be delivered in situ, as we shall see, by a specific delivery means (not shown) according to the specific application. An example application is shown in FIGS. 8a-8c, where the tool 2 is coupled to an endoscope 19, passes through the operating channel 20 and the device 1 to be implanted is housed in a containment pocket 21 applied to the endoscope 19.

In the configuration of the assembly wherein the needle 13 is in a completely extracted position to create the tissue swelling, the connector 15 is intercepted by an internal shoulder 29 of the containment body 6.

In this case as well, when the shoulder 29 intercepts the connector 15, it provides the operator with an indication of having reached the correct position of complete extraction of the needle. The following description refers to the implantation of the device 1 in the intragastric wall, or so-called mucosa. A similar approach may be used for implantation in other sites of the body (human or animal) with the sole replacement of the in situ delivery means, or for the implantation of other devices as long as they are characterised by a shape suitable for operating with the tool 2.

Figure 1A:
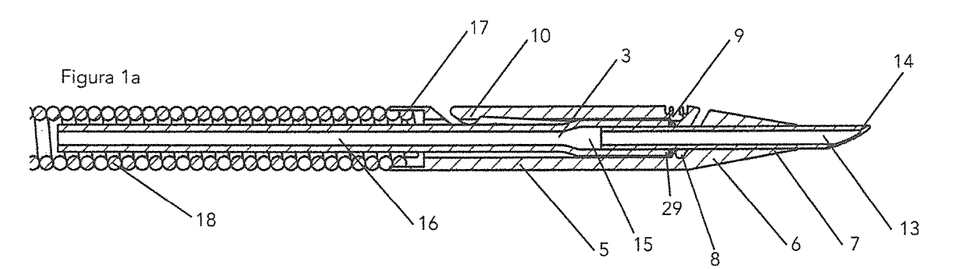
FIGS. 1a-1c show, respectively, a sectional, plan and side elevation view of the implantation tool with the needle in an extracted position and the implant engaged to the pulling element.
Figure 1B:
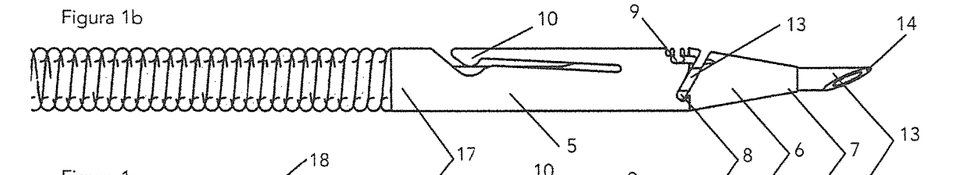
Figure 1C:
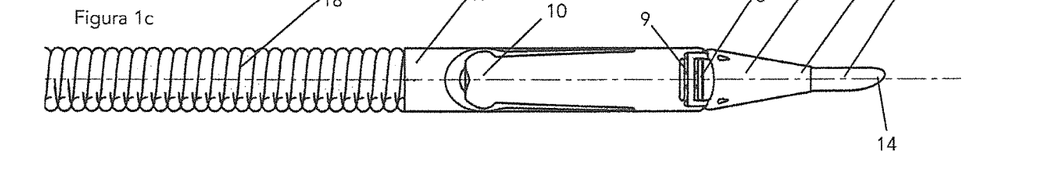

In the positioning shown in FIGS. 1a-1c, the needle 13, thus completely exposed, thanks to its conformation and arrangement, can be brought into contact with the wall in which the implantation will take place, in the gastric mucosa in the example case, is able to penetrate the mucosa by a few millimetres, and allows the injection of the fluid, which is suitable, prevalently but not exclusively, for creating the tissue swelling 4, i.e. sufficient space for the subsequent insertion of the device 1.

The insertion system 5 allows penetration into the tissues thanks to the truncated cone-shaped front end of the containment body 6.

After the creation of the swelling 4 and a sufficient penetration of the insertion system 5 into the tissues, the tool 2 which draws the device 1 is pushed into the tissues thanks to the push exertable by means of the sheath 18.

In order to enable the foregoing, in addition to drawing the device 1, the insertion system 5 must also be able to allow penetration into the tissue by means of the front end of the containment body 6, release the pulling element 11, thus freeing the device 1 once it has reached the implant site, and support the system 3 for creating the tissue swelling 4, whilst the connector 17 with the sheath 18 must be able to allow the tool 2 which draws the device 1 into the tissue to be pushed and directed, ensure the passage of the supply conduit 16, and ensure an adequate movement of the system 3 for creating the tissue swelling such as to free the pulling element 11. For the whole of the first phase of the implantation procedure, before the functions it will perform once the procedure has been completed, the device 1 drawn by the tool 2 thanks to the pulling element 11 is specifically conformed to operate with the implantation tool 2, with the rear, more slender end, turned toward the implant site having a thin morphology which is conformed so as to make the shape of the whole assembly harmonious, and allow the gradual spreading apart of tissues that would otherwise be torn, cut or suffer further unnecessary lesions. The device 1 is endowed with a specific roughness, shape and external composition, with different characteristics from the implant site, specifically to prevent any displacement or bedsores.

The device 1 is preferably conformed so as to pose the least resistance to insertion into the tissue. Irrespective of the specific shape that the device 1 can have depending on the various uses which can be made thereof, it will preferably have, at the slenderer end, if there are size differences between the ends of the device, a flexible plate provided with an eyelet through which, with reference to FIGS. 1-8c, the cable suitable for drawing the device 1 into the tissue swelling, and with reference to FIGS. 9-14, the needle 13, will be made to pass.

If the device 1 does not have said eyelet, the implantation tool 2 can be connected to the device 1 by means of another tool which in any case enables it to be drawn and released in a similar manner to what was previously illustrated.

The in situ delivery means of the tool 2 with the device 1 inside may differ according to the different implant sites.

The in situ delivery means can be an endoscope in the case of insertion into the gastric wall or upper digestive tract: in this case the supply conduit of the fluid 16 and the sheath 18 pass through the operating channel of the endoscope, on the outside of which, in the final part thereof, a housing is inserted to facilitate the delivery of the device 1 into the implantation area. The in situ delivery means may also be defined by a handle that allows the tool 2 to be used with the device 1 inserted in order to insert the device 1 in other areas of the body.

The procedure for using the complete system appears evident from what has been described above and is briefly the following.

The tool 2, with the device 1 connected, is brought in proximity to the tissue where the insertion will take place.

The system 3 is inserted to create the swelling 4 in the soft tissue, e.g. in the gastric mucosa. The fluid with which the swelling 4 is created is injected through the system 3 for creating the swelling 4.

The insertion system 5 is pushed into the soft tissue.

By freeing the pulling element 11, the insertion system 5 deposits the device 1 in the soft tissue. The insertion system 5 is withdrawn.

The device 1 is deposited in the appropriate site.

Upon completion of the implantation, the device 1 will lie completely within the tissues, specifically beneath the mucosa of the stomach.

The body of the device 1 has a shape suitable for implantation; in the case in question it has a cylindrical shape, which is suitable for being introduced into the stomach through the oral cavity with a gastroscope in order to be definitively located in the thickness of the gastric wall. The device can be, for example, a totally implantable electroneuromodulation and/or stimulation device.

The implantation tool thus conceived is susceptible of numerous modifications and variants, all falling within the scope of the inventive concept; moreover, all of the details may be replaced with technically equivalent elements. The materials used, as well as the dimensions, may in practice be of any type, according to needs and the state of the art.

The invention claimed is:

1. An implantation tool (2) for implanting a totally implantable device (1) in the body of a human or animal, comprising:
an axially hollow needle (13) connected to a supply conduit (16) for a fluid injectable from said needle (13) for the creation of a tissue swelling (4), into which said device (1) is introducible;
a longitudinal containment body (6) having inside it an axial cavity along which said needle (13) is slidingly guided; and,
a pulling element (11) disengageably engaged to said containment body (6) for drawing and releasing said device (1) in said tissue swelling (4);
wherein said needle (13) has an extraction position in which it retains said pulling element (11) and is extracted with its tip (14) from the front end of the containment body (6) and a position of partial retraction in which it is completely retracted into the front end of the containment body (6) and retains said pulling element (11), and a position of complete retraction in which it is completely retracted into the front end of the containment body (6) and disengages said pulling element (11).

2. The implantation tool (2) according to claim 1, wherein said needle (13) is floating.

3. The implantation tool (2) according to claim 2, wherein said floating needle (13) is moved by said supply conduit (16).

4. The implantation tool (2) according to claim 1, wherein said containment body (6) has an external cylindrical conformation with a tapered front end for the exit of said needle (13).

5. The implantation tool (2) according to claim 1, wherein said pulling element (11) extends outside said containment body (6).

6. The implantation tool (2) according to claim 1, wherein said pulling element (11) is made up of a cable.

7. The implantation tool (2) according to claim 6, wherein said cable (11) is eyelet-shaped or is an open cable with splices at the ends.

8. The implantation tool (2) according to claim 7, wherein said containment body (6) has a housing seat (8) which crosses said axial cavity so as to releasably retain one end of said cable (12).

9. The implantation tool (2) according to claim 1, wherein said containment body (6) has an elastically yielding stop (10) for stopping said needle (13) in said position of partial retraction into said containment body (6).

10. The implantation tool (2) according to claim 1, wherein said supply conduit (16) is made up of a flexible tube wrapped in a flexible axial stiffening sheath (18).

11. The implantation tool (2) according to claim 10, wherein said sheath (18) is made up of a coil spring.

12. The implantation tool (2) according to claim 1, wherein said pulling element (11) is made up of a flexible plate (23) provided at one end with an eyelet (30) for the passage of said needle (13).

13. An implantation tool (2) for implanting a totally implantable device (1) in the body of a human or animal, comprising:
an axially hollow needle (13) connected to a supply conduit (16) for a fluid injectable from said needle (13) for the creation of a tissue swelling (4), into which said device (1) is introducible;
a longitudinal containment body (6) having inside it an axial cavity along which said needle (13) is slidingly guided; and
a pulling element (11) disengageably engaged to said containment body (6) for drawing and releasing said device (1) in said tissue swelling (4);
wherein said pulling element (11) is made up of a flexible plate (23) provided at one end with an eyelet (30) for the passage of said needle (13).

14. The implantation tool (2) according to claim 13, wherein said containment body (6) has a transverse slot (28) which crosses said axial cavity into which said end of said plate (23) is introducible.

15. The implantation tool (2) according to claim 13, wherein said needle (13) has an extraction position in which it retains said pulling element (11) and is extracted with its tip (14) from the front end of the containment body (6) and a position of partial retraction in which it is completely retracted into the front end of the containment body (6) and retains said pulling element (11), and a position of complete retraction in which it is completely retracted into the front end of the containment body (6) and disengages said pulling element (11).

16. An implantation tool (2) for implanting a totally implantable device (1) in the body of a human or animal, comprising:
an axially hollow needle (13) connected to a supply conduit (16) for a fluid injectable from said needle (13) for the creation of a tissue swelling (4), into which said device (1) is introducible;
a longitudinal containment body (6) having inside it an axial cavity along which said needle (13) is slidingly guided; and
a pulling element (11) disengageably engaged to said containment body (6) for drawing and releasing said device (1) in said tissue swelling (4);
wherein said pulling element (11) is made up of a cable (12), said cable (12) is eyelet-shaped or is an open cable with splices at the ends, and said containment body (6) has a housing seat (8) which crosses said axial cavity so as to releasably retain one end of said cable (12).

17. The implantation tool (2) according to claim 16, wherein said needle (13) has an extraction position in which it retains said pulling element (11) and is extracted with its tip (14) from the front end of the containment body (6) and a position of partial retraction in which it is completely retracted into the front end of the containment body (6) and retains said pulling element (11), and a position of complete retraction in which it is completely retracted into the front end of the containment body (6) and disengages said pulling element (11).

18. An implantation system comprising an implantation tool (2) in accordance with claim 1 and an endoscope (19) provided with an operating channel (20), said tool (2) being configured for a guided sliding along said operating channel (20), said endoscope (19) having an external pocket (21) for containing said device (1).

19. An implantation system comprising an implantation tool (2) in accordance with claim 13 and an endoscope (19) provided with an operating channel (20), said tool (2) being configured for a guided sliding along said operating channel (20), said endoscope (19) having an external pocket (21) for containing said device (1).

20. An implantation system comprising an implantation tool (2) in accordance with claim 16 and an endoscope (19) provided with an operating channel (20), said tool (2) being configured for a guided sliding along said operating channel (20), said endoscope (19) having an external pocket (21) for containing said device (1).

\* \* \* \* \*